United States Patent [19]

Slack

[11] Patent Number: 4,870,866

[45] Date of Patent: Oct. 3, 1989

[54] ULTRASONIC METHOD FOR MEASURING INTERNAL CONTACT PRESSURE BETWEEN MATING SOLID PARTS SEPARATED BY A LIQUID FILM

[75] Inventor: Maurice W. Slack, Edmonton, Canada

[73] Assignee: Centre for Frontier Engineering Research, Edmonton, Canada

[21] Appl. No.: 140,140

[22] Filed: Dec. 31, 1987

[51] Int. Cl.$^4$ ............................................. G01N 29/00
[52] U.S. Cl. ........................................ 73/599; 73/761; 73/778
[58] Field of Search ................ 73/599, 579, 778, 761, 73/581

[56] References Cited

U.S. PATENT DOCUMENTS 3,307,393  3/1967  Kessler ............................... 73/599
4,484,475  11/1984  Ogura et al. ........................ 73/778

OTHER PUBLICATIONS

J. Krautkramer et al., *Ultrasonic Testing of Materials* (Springer-Verlag, New York), 1983, pp. 516–517.

*Primary Examiner*—John Chapman
*Attorney, Agent, or Firm*—Ernest Peter Johnson

[57] ABSTRACT

A method is provided for directly measuring the contact pressure on the mating interfaces of two solids undergoing compression where the interfacial region contains an entrapped film of liquid. An acoustic pulse is directed at either interface. A reference amplitude of the acoustic pulse reflected from the interface is measured as it bears initial contact pressure. A second "loaded" amplitude of the acoustic pulse reflected from the interface is measured when the interface is bearing a different contact pressure. A measure indicative of the change in contact pressure is computed from the ratio of the reference and loaded amplitude measurements by correlation with a calibration curve.

15 Claims, 2 Drawing Sheets

URAP vs. CONTACT PRESSURE CALIBRATION

URAP CONTACT PRESSURE SCAN OF SEAL SURFACE

ULTRASONIC METHOD FOR MEASURING INTERNAL CONTACT PRESSURE BETWEEN MATING SOLID PARTS SEPARATED BY A LIQUID FILM

FIELD OF THE INVENTION

The present invention relates to a non-destructive method for directly measuring the internal contact pressure on the interfaces of two mating solid surfaces undergoing compression when the interfacial region contains an entrapped film of liquid, grease or slurry.

BACKGROUND OF THE INVENTION

Many industrial assemblies involve a thin film of liquid being compressed in the interfacial region between two mating solid surfaces A typical case, in the context of which the present invention was developed, is the 'premium connection' uniting two lengths of oilfield tubing in end-to-end relation. Such a connection comprises two externally threaded pipe ends (pins) screwed tightly into each end of an internally threaded coupling (box). The pins carry annular lands which press against annular lands carried by the boxes to effect circumferential pressure seals remote from the threads. A lubricant/sealant, referred to as thread compound or "dope", is disposed as a thin film between the mating parts. The term 'liquid film' is intended herein to encompass a pure liquid, or a grease, or a slurry of solids in liquid or grease (of which thread compound is an example).

The liquid film is subjected to a normal compressive stress or "contact pressure". Contact pressure can be defined as the compressive stress between two solid bodies, normal to the interface surfaces thereof, which is created by the application of external force to said bodies.

Determining the contact pressure between mating parts is of importance for general stress analysis and in particular for ascertaining the effectiveness of the seal being created. However, present methods for doing this are only of limited usefulness. The methods available can be characterized as 'direct' or 'indirect'.

Indirect methods involve first developing a stress analysis model by photoelastic, analytical or numeric means. A load is then applied to the specimen and external measurements of stress, strain or applied load are made using instruments such as a strain gauge. The stress analysis model and external measurements are then combined to estimate the internal contact pressure of the specimen. These methods can at best give a measure of the average contact pressure and cannot account for variations arising from actual geometrics or other variables versus modelled assumptions. Furthermore few three dimensional effects can be inferred.

There is only one existing direct method available for this purpose, to the applicant's knowledge. This involves neutron diffraction strain measurement The method is directed toward measuring the strain between crystal lattice planes inside the solid parts. If the region examined is directly inside a loaded contact surface, the contact pressure can be inferred from the relationship between strain and stress However this procedure is time consuming to carry out and involves very complex instruments and calculations that are not suited for use outside a specialized laboratory.

So there presently exists a need for a means that can be used in the field to directly measure the internal contact pressure on the surfaces of mating solid parts. In a narrower sense, there exists a need in the oilfield tubing premium connection art for a means that can be used when making up the threaded parts to measure the metal-to-metal sealing surface contact pressures and determine when they reach a desired pre-stress.

The present invention involves the adaption of existing ultrasonic flaw detection technology in a unique way to the problem of directly measuring internal contact pressure.

SUMMARY OF THE INVENTION 2

The present invention is founded on the discovery that a correlative relationship existed between the reflection or transmission amplitude of an acoustic pulse or ultrasonic elastic wave of constant incident amplitude, being directed at a liquid film undergoing compression in the interfacial region between two solid surfaces, and the contact pressure on said solid surfaces. More specifically, it was discovered that the greater the contact pressure on either interface, the greater was the proportion of the incident signal transmitted through the interfacial region. The proportion of the incident signal reflected from the interfacial region was correspondingly reduced. The broad form of the invention was developed from the just described specific discovery.

For purposes of definition herein, and in conformance with the terminology of the art, the ratio of transmitted amplitude to incident amplitude is called the "transmission coefficient" and the ratio of reflected amplitude to incident amplitude is called the "reflection coefficient".

The discovered relationship is based upon the following understandings. The energy of the elastic wave is related to variations of the pressure and displacement amplitudes in the elastic medium. When referenced to the incident wave amplitude, the amplitude variations of an elastic wave reflected from or transmitted through a thin liquid film entrapped between two solids essentially depends upon variations in the film properties and not on the metal or other boundary materials properties. These film properties are the film thickness and internal properties of the film material, namely the speed of sound therein and the density thereof. Therefore, according to these understandings, the reflection and transmission coefficient will vary as function of the contact pressure being carried by the solid surfaces because the film properties are influenced by this contact pressure. Thus, by maintaining a constant incident amplitude reference and by measuring the reflection amplitude before and after the application of a pressure change thereto, the change in reflection coefficient due to the internal contact pressure change can be established. If one of these amplitudes is obtained when the solid surfaces are at zero pressure, the absolute contact pressure can be indicated.

In accordance with a preferred embodiment of the present invention, a method is provided for determining contact pressure wherein a thin liquid film is undergoing compression in the interfacial region between two solid surfaces, which method comprises: directing an acoustic pulse of constant incident amplitude at either solid interface; establishing a measure of the reference reflection coefficient of the interface therein, which reference is indicative of the incident amplitude (if the reference is being established at zero contact pressure, the condition of the interface may be defined with or without the film material present, and with or without the two bodies in intimate contact); establishing a measure of the reflection coefficient of the interface when the interface is bearing a different contact pressure; and computing from the reference and loaded measurements a measure indicative of the change in contact pressure.

The change in contact pressure can similarly be indicated by directing an acoustic pulse of constant incident amplitude at either solid interface and establishing a measure of the transmission coefficients of the interfacial region at reference and loaded conditions.

In another aspect of the invention, a measure of the reflection coefficient or transmission coefficient can be established by directing an acoustic pulse at either solid interface and controlling the incident amplitude of said pulse to maintain the reflected amplitude or transmitted amplitude constant. A measure of the incident amplitude can therefore be used to establish a measure of the reflection coefficient or transmission coefficient in the reference and loaded conditions.

In a further aspect of the invention, a measure of the reflection coefficient or transmission coefficient can be established by directing an acoustic pulse at either solid interface and establishing a measure of the reflected amplitude and transmitted amplitude of said pulse. This is possible because the reflected pulse energy plus the transmitted pulse energy equal the incident pulse energy. A measure of the reflected and transmitted amplitudes can therefore be used to establish a measure of the reflection coefficient or transmission coefficient in the reference and loaded conditions.

By providing a calibration curve which correlates a range of measured contact pressures with a corresponding range of measures of reflection or transmission coefficients, an absolute measure of the contact pressure on the mating solid interfaces undergoing compression may thereby be obtained.

The same procedure for establishing reference coefficients must be followed when establishing the calibration curve and measuring contact pressure. Specifically, both measurements may be taken either with the film material present or not with the two bodies in intimate contact or not.

Broadly stated, the invention comprises a method for determining a measure of contact pressure wherein a thin liquid film is undergoing compression in the interfacial region between two solid surfaces, said film forming a part of the interfacial region, comprising: directing an acoustic pulse at said thin liquid film; and establishing a measure of the reflection coefficient or transmission coefficient of the interfacial region to provide the measure of contact pressure.

DESCRIPTION OF THE PREFERRED EMBODIMENT

Whilst the description of the determination of thin film contact pressure given herein refers specifically to the make-up of premium tubing connections, it will be readily understood that the scope of the invention encompasses measurement of contact pressure in any thin liquid film undergoing compression between two solid bodies.

Figure 1:
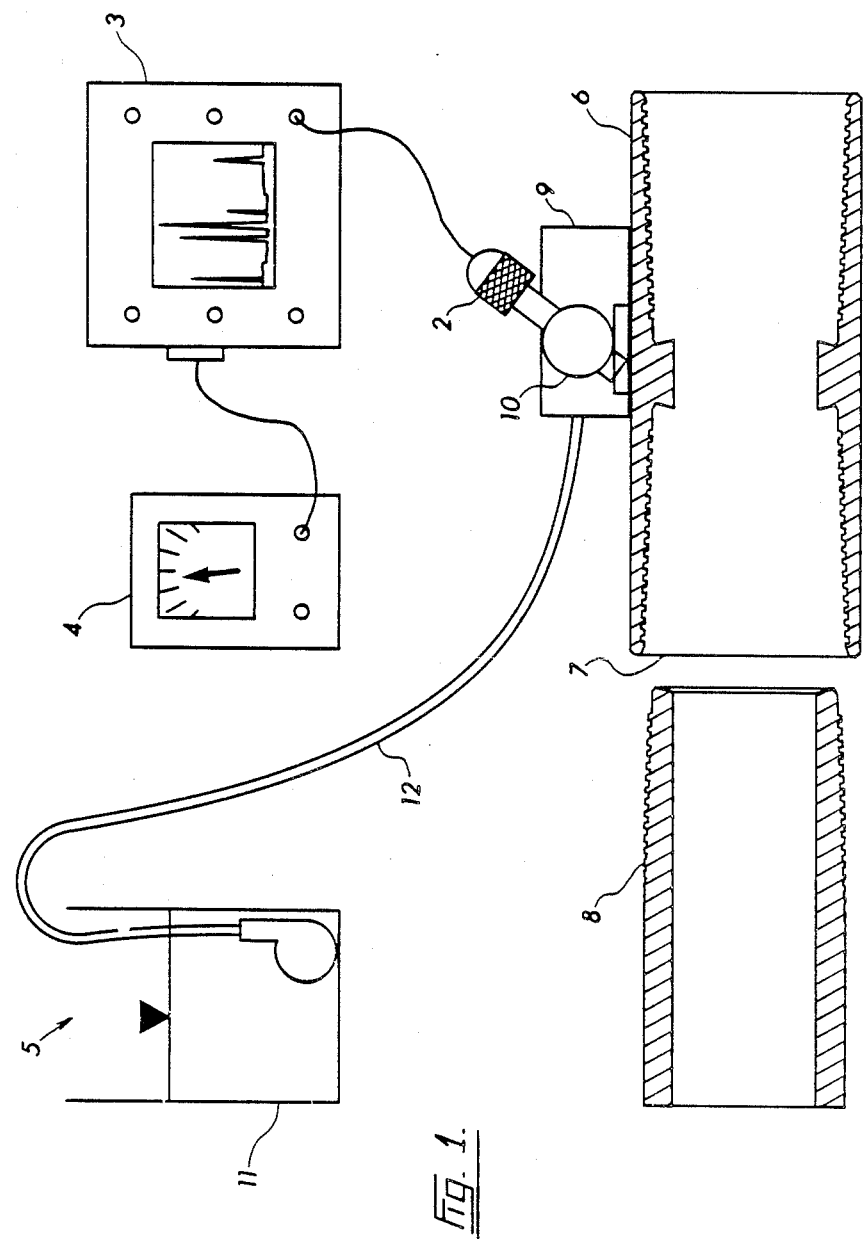
FIG. 1 is a schematic diagram of the apparatus utilized in carrying out the method of the present invention.

Turning to FIG. 1, there is shown the apparatus used for the measurement of contact pressure where a thread compound (API Modified, where API is the American Petroleum Institute) film was compressed between "metal-to-metal" surfaces in a tubing premium connection. The apparatus included an ultrasonic probe 2, an ultrasonic flaw detector (UFD) 3, a recorder 4, and a water supply system 5. The apparatus was used to determine contact pressure at the contacting surface "x" within a tubing connection 6 consisting of a box 7 and pin 8.

The ultrasonic probe 2 was mounted on a positioning jig 9, to hold it in the correct position on, and in correct orientation to, the tubing box 7. The ultrasonic probe 2 used was a commercially available unit obtained from Harisonic Laboratories Inc., Stamford, Conn. The details of the probe were: model number I2, 1502T, having a diameter: 3.2 mm (0.125 in), Focusing: $Y_o = 25.4$ mm (1.00 in) and operating at a frequency of 15 MHz. The piezoelectric crystal source of the probe 2 was functional to transmit an acoustic wave pulse of constant amplitude upon application of a voltage pulse from UFD 3 and subsequently return a voltage proportional to acoustic amplitude upon receiving a reflected acoustic pulse.

Positioning jig 9 included a rotatable probe-receiving drum 10. The drum 10 was adapted to receive a flow of water, which water was in contact with the piezoelectric crystal of probe 2 and the tubing box 7. The water was pumped to the drum 10 from a low pressure water supply tank 11 via a conduit 12. The water functioned as an acoustic couplant between the probe 2 and the coupling 6.

UFD 3 was electrically connected to probe 2. UFD 3 was equipped with a linear gated peak reader amplitude output, and gain and frequency control. The unit used was Model USL 48, obtained from Krautkramer Branson, Lewistown, Pa. It functioned to provide a linear measure of the peak amplitude of the gated acoustic pulse.

The recorder 4 was electrically connected to the UFD 3. The recorder 4 measured the voltage output corresponding to the gated peak reader output. One recorder used was a commercially available digital voltmeter compatible with the UFD amplitude gate output.

In operation, the instruments were connected up in accordance with FIG. 1. Probe 2 was positioned in the positioning jig 9 and focused on the clean metal surface of the box 7, so that the acoustic beam to be reflected was to be obtained from the internal seal surface "X" at which the stress was to be measured. Compressional waves were used, although shear waves could also be used.

The gain and amplitude gate of the detector 3 was adjusted to measure the amplitude of the reflection coming from surface "X" and the detector output was recorded by the recorder 4. Thus the reflected signal amplitude, taken by a measure of the voltage output from the gated reflection amplitude peak reader on the detector 3, reflected from the metal surface "X" of the box 7, without the application of thread compound thereto and without intimate contact of the pin surface, was determined. These 'free surface reflection amplitudes' ($V_{fi}$), obtained at several circumferential positions around the box, were the initial reference amplitude measurements.

API Modified thread compound was applied to the thread and sealing surfaces of the pin 8 and/or box 7, and the pin was screwed into the box. The seal surface "X" was loaded as a result, compressing the film between the solid steel-to-steel surfaces. Reflected signal amplitudes ($V_{li}$) were recorded from the loaded seal surface at the same circumferential positions as $V_{fi}$.

Stated otherwise, the procedure followed comprised obtaining a set of reference reflection amplitude measurements ($f_i$) at certain locations around the specimen seal surface while it was clean, unloaded, and exposed to the atmosphere only. A second set of readings ($l_i$) taken (with an acoustic pulse providing the same incident amplitude) at the same locations with the surfaces loaded and the film present were then expressed as a portion of or ratio ($r_i$) of the free surface readings. This was the 'reflection amplitude ratio' and it is expressed mathematically by:

$$r_i = \frac{l_i}{f_i}$$

where,
$r_i$ = reflection amplitude ratio at a circumferential location "i";
$l_i$ = loaded reflection amplitude at "i" for any contact pressure; and
$f_i$ = reference reflection amplitude at "i" which may be any measure in constant proportion to the incident acoustic amplitude when $l_i$ was obtained.

By positioning a transmitting probe 2 internally (or externally) of box 7 and having the receiver of the UFD on the outside (or inside) of the specimen and measuring the change in amplitude of the transmitted pulse upon application of contact pressure to the thin liquid film, a measure indicative of the contact pressure thereof may be also established.

Because the raw voltage outputs from recorder 4 are proportional to the acoustic pulse amplitude, the ratio $r_i$ can be calculated from the raw voltage outputs as follows:

$$r_i = \frac{V_{li}}{V_{fi}},$$

where
$V_{li}$ = "raw" loaded reflection signal voltage at "i" (voltage output from the gated reflection amplitude peak reader on UFD normalized to the same gain as used for obtaining $V_{fi}$) for any contact pressure; and
$V_{fi}$ = "raw" reference reflection signal voltage at "i", from the free surface (normalized for any incident amplitude changes).
URAP (dB) = 20 log ($r_i$) (termed URAP measurement) expresses the ratio $r_i$ in decibels.

The ratio method acts to provide a consistent incident energy reference and to normalize the URAP measurement for amplitude changes that may occur due to extraneous variables not associated with changes in the reflection or transmission coefficient of the seal surface. Examples of extraneous variables along the signal path are surface irregularities or inclusions in the solid body. Such normalization may not be necessary in all cases: in ideal circumstances, the change in contact pressure is calculable directly from the amplitude $l_i$, if a calibration curve has been constructed relating $l_i$ and contact pressure.

In order to obtain an absolute measure of the contact pressure of the test specimen it was necessary to first provide a calibration curve which correlates a range of measured contact pressures with a corresponding range of URAP measurements. To this end, a calibration jig (not shown) was provided which was functional to apply a known force on two mating steel surfaces of known surface area where the interfacial region contained an entrapped thread compound film. The corresponding URAP measurement at each increment of applied force was obtained using the instrumentation described herein. The absolute contact pressure was determined using the relationship $$\text{Contact Pressure} = \frac{\text{Force}}{\text{Area}}.$$

The URAP measurement is a function of several independent variables namely, the acoustic pulse frequency, surface roughness, rotation and composition of the lubricant. Thus, the experimental studies were necessarily parametric.

The following examples taken in conjunction with the results plotted in the accompanying figures demonstrate the operability of the present invention.

EXAMPLE I

Figure 2:
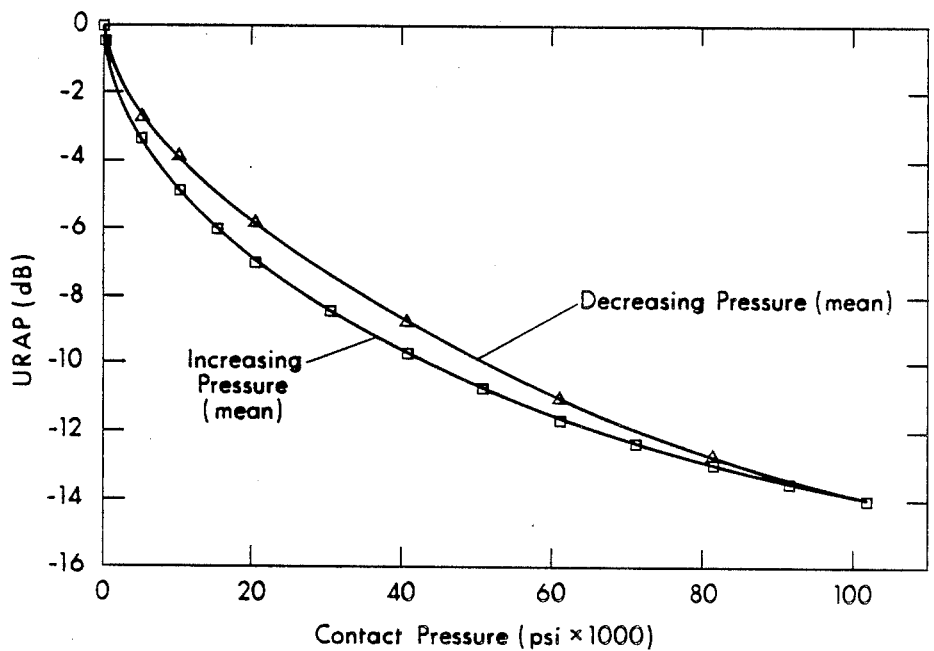
FIG. 2 is a plot of the ultrasonic reflection amplitude ratio expressed in decibels versus contact pressure (i.e. a calibration curve)

This example is provided to demonstrate the relationship between the URAP measurement and contact pressure in a calibration specimen. A 15 MHz ultrasonic probe was utilized. To simulate typical interfacial roughness of tubing seal surfaces the calibration specimen was machined to a surface roughness of $1.52 \times 10^{-3}$ mm. To approximate typical sliding shear in the film during make-up, the bottom portion of the calibration specimen was rotated in relation to the proportion. Rotation was increased as contact pressure increased: rotation was input at 0.66 mm/169 kPa (0.026 in/10,000 psi) of contact pressure. The plot of the URAP measurement versus contact pressure is given in FIG. 2 appended hereto.

This example demonstrates that the amplitude of elastic waves reflected from or transmitted through a thin film of compressible liquid, disposed between two solid bodies and bearing contact pressure, depends on this contact pressure.

EXAMPLE II

The specimen used for this example was a standard 89 mm 13.7 kg/m premium tubing connection as manufactured by VAM Canada Ltd. A 15 mHz probe was installed in the positioning jig, acoustically coupled to the metal surface of the specimen, and focused on the seal surface therein. The reference reflection amplitude of the specimen was measured at several arbitrarily selected locations around the circumference. Similar reflection amplitude measurements were made when the connection was made up. The URAP measurement was computed as discussed above and converted to contact pressure based on the correlative relationship shown in FIG. 2.

Figure 3:
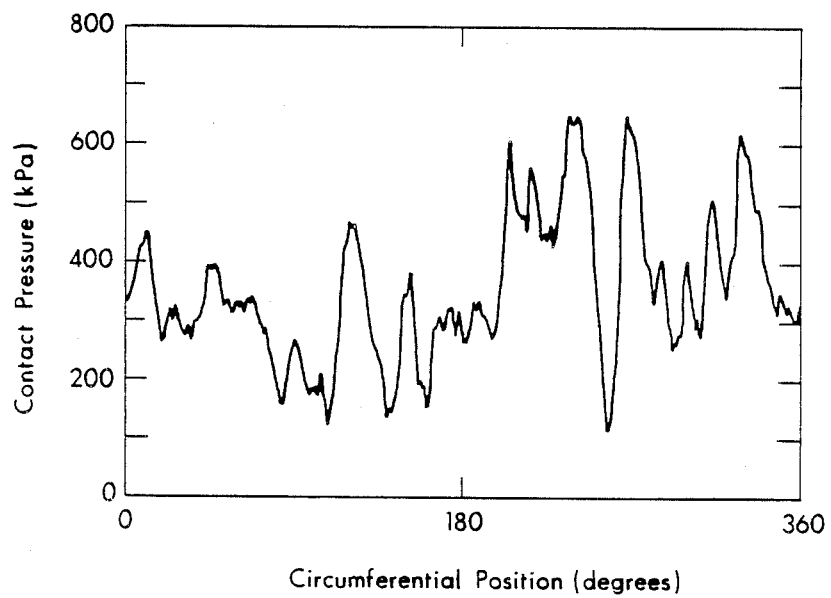
FIG. 3 is a scan of the contact pressure (derived from the calibration curve of FIG. 2) around the circumference of a premium connection seal after make-up.

The results are given in FIG. 3 attached hereto, which shows the seal surface contact pressure around the circumference of the connection.

The embodiments of the invention in which an exclusive property or privilege is claimed are defined as follows:

1. A method for determining a measure of contact pressure wherein a thin liquid film is undergoing compression in the interfacial region between two solid surfaces, said film having been applied to one or both of the solid surfaces prior to compression of the film by the solid surfaces, said film forming a part of the interfacial region, comprising:
   directing an acoustic pulse at said thin compressed liquid film; and
   establishing a measure or measures of the reflection coefficient or transmission coefficient of the interfacial region to provide the measure of contact pressure.

2. A method for determining a measure of contact pressure wherein a thin liquid film is undergoing compression in the interfacial region between two solid surfaces, said film having been applied to one or both of the solid surfaces prior to compression of the film by the solid surfaces, said film forming a part of the interfacial region, comprising:
   directing an acoustic pulse of constant incident amplitude at said thin compressed liquid film; and
   establishing a measure or measures of the amplitude of the acoustic pulse reflected or transmitted therethrough, which is a measure of the reflection coefficient or transmission coefficient, to thereby provide the measure of contact pressure.

3. A method for determining a measure of contact pressure wherein a thin liquid film is undergoing compression in the interfacial region between two solid surfaces, said film having been applied to one or both of the solid surfaces prior to compression of the film by the solid surfaces, said film forming a part of the interfacial region, comprising:
   directing an acoustic pulse at said thin compressed liquid film and controlling the incident amplitude of said pulse to maintain constant one of the reflected or transmitted amplitudes; and
   establishing a measure or measures of the incident amplitude, which is a measure of the reflection coefficient or transmission coefficient, to thereby provide the measure of contact pressure.

4. A method for determining a measure of contact pressure wherein a thin liquid film is undergoing compression in the interfacial region between two solid surfaces, said film having been applied to one or both of the said surfaces prior to compression of the film by the solid surfaces, said film forming a part of the interfacial region, comprising:
   directing an acoustic pulse at the said thin compressed liquid film;
   establishing a measure or measures of the amplitude of the acoustic pulse reflected therefrom;
   establishing a measure of the amplitude of the acoustic pulse transmitted therethrough; and
   establishing from said measurements a measure of the reflection coefficient or the transmission coefficient, to thereby provide the measure of contact pressure.

5. A method for determining a measure of contact pressure wherein a thin liquid film is undergoing compression in the interfacial region between two solid surfaces, said film having been applied to one or both of the said surfaces prior to compression of the film by the solid surfaces, said film forming part of the interfacial region, comprising:
   (a) directing an acoustic pulse at either solid interface;
   (b) establishing a measure or measures of the reflection coefficient or transmission coefficient of the acoustic pulse reflected therefrom or transmitted therethrough;
   (c) changing the contact pressure on the interfacial region;
   (d) directing an acoustic pulse at the thin compressed liquid film and establishing a measure of the reflection coefficient or transmission coefficient of the loaded interfacial region; and
   (e) computing from the references and loaded reflection coefficients or transmission coefficients a measure indicative of the change in contact pressure.

6. A method as set forth in claim 5 wherein:
   the acoustic pulses of steps (a) and (d) are of constant incident amplitude.

7. A method as set forth in claim 5 comprising:
   controlling the incident amplitude of each of the acoustic pulses of steps (a) and (d) to maintain constant one of the reflected or transmitted amplitudes; and wherein
   the measure of reflection coefficient or transmission coefficient in steps (b) and (d) is established by monitoring the incident amplitude.

8. A method as set forth in claim 5 wherein:
   the measures of steps (b) and (d) are each established by obtaining measures of the amplitude of the acoustic pulse reflected therefrom and the amplitude of the acoustic pulse transmitted therethrough.

9. The method as set forth in claim 1 wherein:
   the thickness of the interfacial region is less than about 0.5λ of the acoustic pulse where λ is the wavelength of the acoustic pulse in the thin liquid film.

10. The method as set forth in claim 5 wherein:
    the thickness of the interfacial region is less than about 0.5λ of the acoustic pulse where λ is the wavelength of the acoustic pulse in the thin liquid film.

11. The method as set forth in claim 1 wherein:
    the acoustic pulse comprises a compression wave.

12. The method as set forth in claim 5 wherein:
    the acoustic pulse comprises a compression wave.

13. The method as set forth in claim 1 wherein:
    the thickness of the interfacial region is less than about 0.5λ of the acoustic pulse where λ is the wavelength of the acoustic pulse in the thin liquid film; and
    the acoustic pulse comprises a compression wave.

14. The method as set forth in claim 5 wherein:
    the thickness of the interfacial region is less than about 0.5λ of the acoustic pulse where λ is the wavelength of the acoustic pulse in the thin liquid film; and
    the acoustic pulse comprises a compression wave.

15. A method for determining contact pressure of sealing surfaces during or after make-up of an oilfield tubular connection having pin and box parts and having a thin liquid film of thread compound undergoing compression between the sealing surfaces, which method comprises:

directing an acoustic pulse through an acoustic couplant at a sealing surface of the connection and measuring the reflection amplitude thereof to obtain a measure indicative of the reference reflection coefficient;

applying load to the sealing surfaces with the parts made up and the thin liquid film being compressed therebetween;

directing an acoustic pulse through a couplant at the loaded sealing surfaces and obtaining a measure indicative of the reflection coefficient; and establishing, from the measures of the reference reflection coefficient and the loaded reflection coefficient, a measure indicative of the contact pressure on the mating surfaces being compressed.

* * * * *